United States Patent [19]

Knöfel et al.

[11] Patent Number: 4,603,189
[45] Date of Patent: Jul. 29, 1986

[54] TRIISOCYANATES AND A PROCESS FOR THEIR PREPARATION

[75] Inventors: Hartmut Knöfel, Odenthal; Stefan Penninger, Pulheim; Michael Brockelt, Bergisch-Gladbach; Günter Hammen, Rommerskirchen; Herbert Stutz, Dormagen, all of Fed. Rep. of Germany

[73] Assignee: Bayer Aktiengesellschaft, Leverkusen, Fed. Rep. of Germany

[21] Appl. No.: 728,351

[22] Filed: Apr. 29, 1985

[30] Foreign Application Priority Data

May 12, 1984 [DE] Fed. Rep. of Germany ....... 3417684

[51] Int. Cl.$^4$ ............................................. C08G 18/74
[52] U.S. Cl. ...................................... 528/67; 528/68; 528/76; 528/83; 528/85
[58] Field of Search ..................... 528/67, 68, 76, 83, 528/85; 260/453 PH, 453 AP, 453 R

[56] References Cited

U.S. PATENT DOCUMENTS 2,729,666 1/1956 Stallmann et al. ................... 260/453
3,645,979 2/1972 Liebach et al. ............. 260/77.5 NC
3,663,514 5/1972 Campbell et al. ................. 260/77.5

FOREIGN PATENT DOCUMENTS 1171097 7/1984 Canada .
0113043 11/1984 European Pat. Off. .
0113044 11/1984 European Pat. Off. .
1080739 8/1967 United Kingdom .

OTHER PUBLICATIONS

H. Wagner, H. F. Sarx, "Lackkunstharze", Carl Hanser Verlag, Munich, 5th Edition, 1971, pp. 163–164.

Primary Examiner—Maurice J. Welsh
Attorney, Agent, or Firm—Gene Harsh; Joseph C. Gil; Lyndanne M. Whalen

[57] ABSTRACT

Triisocyanates and isomeric mixtures of triisocyanates corresponding to the formula

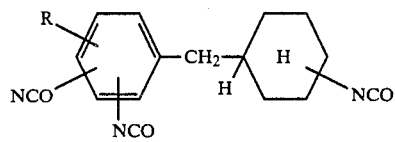

in which
R represents hydrogen or an alkyl group having from 1 to 4 carbon atoms are made by phosgenating the corresponding triamine. These triisocyanates are particularly useful in the production of polyurethanes, especially polyurethane lacquer coats.

7 Claims, No Drawings

TRIISOCYANATES AND A PROCESS FOR THEIR PREPARATION

BACKGROUND OF THE INVENTION

This invention relates to triisocyanates which contain both aromatically and cycloaliphatically bound isocyanate groups and to a process for their preparation.

Araliphatic polyisocyanates such as the isocyanate group-containing mixed primer of hexamethylene diisocyanate and diisocyanatotoluene are eminently suitable for the production of polyurethanes (particularly polyurethane lacquer coats) because the positive properties of aromatic isocyanates combine advantageously with those of aliphatic isocyanates. Polyurethane lacquers based on such araliphatic lacquer polyisocyanates are distinguished by the following advantageous properties (see H. Wagner, H. F. Sarx, "Lackkunstharze", publishers Carl Hanser Verlag, Munich, 5th Edition, 1971, pages 163-164): (1) rapid drying; (2) increased resistance of the lacquer coats to yellowing compared with those based on aromatic polyisocyanates; (3) increased reactivity and hence shorter drying times compared with corresponding lacquers based on aliphatic polyisocyanates; (4) good stability of the color shade of pigmented lacquers; (5) improved gloss retention and weathering resistance compared with corresponding lacquers based on aromatic polyisocyanates and (6) relatively long pot life of the lacquers.

The preparation of such araliphatic polyisocyanates by methods such as that described in German Patentschrift No. 1,670,667 is, however, rather involved, because the excess starting diisocyanates present after trimerization must be removed in an additional process step. Another disadvantage of such methods is that the trimerization reaction uses up valuable isocyanate groups. Further, the mixed trimers formed by these processes cannot be purified by distillation after their preparation.

SUMMARY OF THE INVENTION

It is an object of the present invention to provide new triisocyanates containing both aromatically and cycloaliphatically bound isocyanate groups.

It is also an object of the present invention to provide triisocyanates having isocyanate groups with different reactivities.

It is another object of the present invention to provide triisocyanates which are useful in the production of polyurethane lacquers having the advantageous properties of known lacquer polyisocyanates without the disadvantages of those known polyisocyanates.

It is a further object of the present invention to provide a relatively simple process for the production of triisocyanates containing both aromatically and cycloaliphatically bound isocyanate groups.

These and other objects which will be apparent to those skilled in the art are accomplished by triisocyanates corresponding to the formula

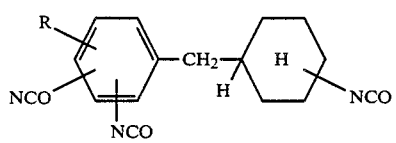
(I)

in which
R represents hydrogen or an alkyl group having from 1 to 4 carbon atoms.

These triisocyanates are made by phosgenating triamines corresponding to the formula

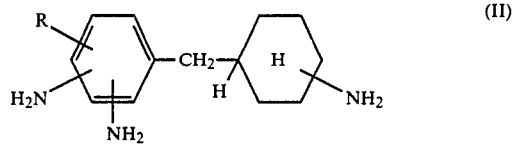
(II)

in which R is as defined above.

DETAILED DESCRIPTION OF THE INVENTION

The present invention relates to triisocyanates corresponding to the following formula, optionally constituting position and/or stereoisomeric mixtures:

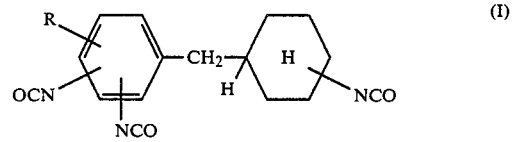
(I)

in which
R represents hydrogen or a branched chain or linear alkyl group having 1 to 4 carbon atoms, preferably hydrogen or a methyl group.

The invention also relates to a process for the preparation of these triisocyanates in which the polyamines on which the isocyanates are based are phosgenated.

Lastly, the invention also relates to the use of these triisocyanates as starting components for polyurethanes by the isocyanate polyaddition process. These triisocyanates may be reacted with any of the isocyanate-reactive group containing materials known to those in the art.

The starting materials for the process of the present invention are the polyamines on which the polyisocyanates according to the invention are based. These polyamines are triamines corresponding to the following formula, optionally in the form of mixtures of position and/or stereoisomers:

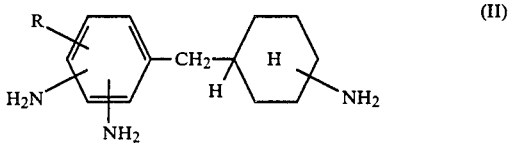
(II)

in which
R has the same meaning as above.

The starting materials used for the preparation of the polyamines II used in the process according to the invention are the corresponding aromatic triamines corresponding to formula (III)

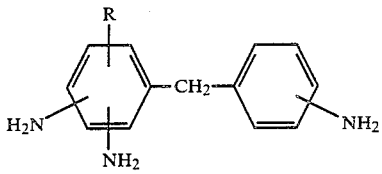

(III)

in which
R has the same meaning as above.

The preparation of these aromatic triamines corresponding to formula III may be carried out in known manner. For example, N-[4(2)-aminobenzyl]aniline may be reacted with optionally alkyl-substituted phenylene diamines according to Beilstein 13 H, page 309 or according to German Patentschrift No. 107,718. Triamines corresponding to formula III may also be made by reacting (i) a 3- or 4-nitrobenzylhalide, benzyl alcohol or a nitrobenzylchloride isomeric mixture with (ii) nitrobenzene, alkyl-substituted nitrobenzene, alkyl benzene or benzene in the presence of a Friedel-Crafts or acid catalyst, nitration of the resulting reaction products to the corresponding trinitro compounds and hydrogenation of the nitro groups by a process analogous to that disclosed in European Patent Application No. 46,917. The trinitro compounds obtained by the last-mentioned method and the aromatic triamines prepared from them constitute technical mixtures which, due to the method of preparation, may still contain difunctional compounds in addition to the appropriate trifunctional compounds. The small proportion of difunctional compounds present in these technical mixtures may, however, be removed by distillation at the amine stage if desired.

The following are typical examples of suitable starting materials corresponding to formula III for the preparation of triamines corresponding to formula II:
2,4,4'(2')-triaminodiphenylmethane,
2,6,4'(2')-triaminodiphenylmethane,
4,6,4'(2')-triamino-3-methyl-diphenylmethane,
2,6,4'(2')-triamino-3-methyl-diphenylmethane,
3,5,4'(2')-triamino-4-methyl-diphenylmethane,
2,6,4'(2')-triamino-4-methyl-diphenylmethane,
3,5,4'(2')-triamino-2-methyl-diphenylmethane,
4,6,4'(2')-triamino-2-methyl-diphenylmethane and mixtures thereof. The corresponding ethyl, isopropyl, n-propyl or n-, iso- or tert-butyl-substituted triaminodiphenylmethanes may also be used.

The preferred starting materials corresponding to formula III are isomeric mixtures of methyl-substituted triaminodiphenylmethanes or commercial mixtures thereof with the corresponding diamines such as those obtained from the trinitration of 2- and/or 4-methyl-diphenylmethane, or of hydrocarbon mixtures make up of those isomers, and reduction of the nitro groups optionally followed by working up of the reaction product by distillation. The particularly preferred starting materials prepared by this procedure are generally made up of more than 80 wt % of triaminodiphenylmethanes which in turn are made up of over 90 wt % of aminobenzyl-diamino-toluene isomers.

As has been mentioned above, the starting materials may be exclusively aromatic triamines corresponding to formula III or mixtures of such triamines. They may also be mixtures of such triamines with the corresponding diamines (preferably diamines having an amino group on each aromatic ring). These mixtures may contain up to 90 wt %, preferably up to 50 wt % and most preferably up to 20 wt % of such diamines, based on the whole mixture. Polyamine mixtures which contain a high proportion of such aromatic diamines due to the method of their preparation may be substantially or completely freed from the diamines by distillation before the starting materials for the process of the present invention are prepared by partial hydrogenation of the aromatic polyamines. Alternatively, the aromatic polyamine mixtures may be directly subjected to partial hydrogenation and the partially hydrogenated polyamine mixtures may then optionally be freed from the diamines and other by-products resulting from hydrogenation before being used to produce the triisocyanates of the present invention. Alternatively, distillative separation of difunctional reaction products (obtained by phosgenation of the corresponding diamines) and optionally other by-products may be carried out after the phosgenation process of the present invention to yield substantially pure polyisocyanates of formula (I).

Hydrogenation of the aromatic triamines on the nucleus may be carried out by methods known in the art. One such method is described in U.S. Pat. No. 2,511,028. In this procedure, the aromatic diamines, optionally present as mixtures with the corresponding diamines, are catalytically hydrogenated so that 3 mol of hydrogen are added for each mol of starting compound. (The term "starting compound" includes mixtures of triamines with diamines). This means that the hydrogenation reaction is preferably stopped after 3 mol of hydrogen have been used up for each mol of starting compound. This hydrogenation is carried out at 20° to 300° C., preferably at 70° to 200° C., in particular at 120° to 150° C., under a pressure of 20 to 300 bar, preferably 200 to 300 bar.

The hydrogenation reaction is carried out in the presence of a hydrogenation catalyst put into the process in a quantity of from 0.1 to 20 wt %, preferably from 0.1 to 10 wt %, based on catalytically active metal and triamine compounds.

Examples of suitable catalysts include elements of the 8th sub-Group of the Periodic System of Elements or catalytically active organic compounds of these elements, optionally on inert carriers such as active charcoal, silica gel or, in particular, aluminum oxide. Particularly suitable catalysts are, for example, ruthenium, platinum, rhodium, nickel and/or cobalt catalysts either in elemental form or chemically bound. Ruthenium and catalytically active ruthenium compounds are particularly preferred. The following are examples of suitable ruthenium compounds: ruthenium dioxide; ruthenium tetroxide; barium perruthenite; sodium, potassium, silver, calcium and magnesium ruthenate; sodium perruthenate; ruthenium pentafluoride; ruthenium tetrafluoride hydrate and ruthenium trichloride. If carrier substances are used for the catalysts, the metal content of the carrier catalyst is generally from 1 to 10 wt %, preferably from 1 to 5 wt %. The nature and quantity of the catalyst used is otherwise, of course, in no way critical to the invention since the hydrogenation reaction is carried out by methods known in the art.

It is often advisable to carry out the hydrogenation reaction in the presence of ammonia since ammonia suppresses undesirable deamination reactions which would result in the formation of secondary amines as by-products. If ammonia is used, this is generally added in quantities of from 0.1 to 30 wt %, preferably from 5 to 10 wt %, based on the starting materials which are to be hydrogenated.

The hydrogenation may be carried out in the absence of solvent or in the presence of inert solvents. Low melting or liquid diamines are generally hydrogenated solvent-free while high melting diamines are hydrogenated in the form of solutions. Suitable solvents for this purpose are organic compounds with a low boiling point which are inert under the reaction conditions, particularly alcohols such as methanol, ethanol, n-propanol, i-propanol and t-butanol; ethers such as dioxane, tetrahydrofuran; diethylether; and hydrocarbons such as cyclohexane. Hydrogenation may be carried out, for example, continuously in a reaction tube or a cascade of pressure vessels or, preferably, discontinuously in a stirrer autoclave. In the last case, the autoclave is charged with catalyst, the substance to be hydrogenated and optionally a solvent. The autoclave is flushed repeatedly with inert gas and ammonia is then added if indicated. Hydrogen is then forced in, the mixture is heated to the reaction temperature and hydrogenation is carried out until the theoretically required quantity of hydrogen has been absorbed. After cooling of the reaction mixture and separation of the catalyst, the hydrogenation product may be worked up by distillation.

The hydrogenation products are obtained in high yields and may, if necessary, be separated by distillation from unreacted aromatic amines or from perhydrogenated diamines and triamines which are formed as by-products and from the corresponding partially hydrogenated diamines. Even when the triamines corresponding to formula (II) used for the process according to the invention have been prepared pure by such methods of distillation, they are generally mixtures of stereoisomers and possibly position isomers. Triamines made up of over 80 wt %, preferably over 95 wt % of polyamines corresponding to general formula (II) may be obtained by employing the method of working up by distillation indicated above. Polyamines which have not been worked up by distillation still constitute suitable starting materials for the purpose of the invention. However, these undistilled polyamines may contain not only position and or stereoisomeric mixtures but also up to 90 wt %, preferably up to 50 wt % and in particular up to 20 wt % of other, optionally alkyl-substituted, di- and/or triamines having a diphenylmethane, benzyl cyclohexane or dicyclohexyl methane structure. The above mentioned diamines may be present if the aromatic triamines used as starting materials contain aromatic diamines, and/or if a certain amount of deamination of the cycloaliphatic ring takes place during the hydrogenation reaction. Such deamination may, however, be deterred by the addition of ammonia during the hydrogenation reaction.

On the basis of NMR spectroscopic investigations it was found that when alkyl substituted aromatic triamines are used as starting material for carrying out hydrogenation, the alkyl substituents are present almost exclusively on the aromatic ring of the hydrogenation products.

Purification of the hydrogenation products by distillation before they are used in the phosgenation process of the present invention is generally not necessary because the phosgenation products may optionally be worked up by distillation after the phosgenation reaction. Equally, the suitability of the hydrogenation products for use in the phosgenation process of the present invention does not depend upon their position or stereoisomerism or on the distribution of these isomers.

The aromatic-cycloaliphatic triamines produced by hydrogenation of the above-mentioned aromatic triamines are typical examples of suitable starting polyamines for the process of the present invention. As already mentioned, these starting polyamines may, if desired, be freed by distillation from the by-products often formed in the course of the hydrogenation reaction. These by-products include not only the diamines with a benzyl-cyclohexane structure formed by deamination but also di- and/or triamines with a diphenylmethane or dicyclohexylmethane structure which are liable to occur in admixture with the triamines of formula (II) due to the partial hydrogenation not proceeding strictly selectively. Apart from these limitations, the starting polyamines to be used in the process of the invention correspond to the above exemplified aromatic polyamines or polyamine mixtures used for their preparation.

In the process of the invention for the preparation of the new triisocyanates, phosgenation of the starting amines or of their salts is carried out by known methods in the presence of an inert organic solvent (see Houben-Weyl, Methoden der organischen Chemie, Georg Thieme Verlag Stuttgart (1952), Volume 8, 4th Edition, pages 120 et seq). In accordance with the description given above, the term "starting amines" used in this context to include both pure compounds of the general formula (II), optionally as position and/or stereoisomeric mixtures, and mixtures of these compounds containing up to 90 wt %, preferably up to 50 wt % and in particular up to 30 wt % of other, optionally alkyl-substituted diamines and/or triamines having a diphenylmethane, benzylcyclohexyl or dicyclohexyl methane structure. The percentages given are based in each case on the total mixture.

The salts to be phosgenated are preferably hydrochlorides or ammonium carbamates obtained by saturation of the polyamine solutions with gaseous hydrogen chloride or carbon dioxide, but other salts may in principle also be used for phosgenation, for example, salts obtained by neutralization of the polyamines with acids which split off protons.

The selectivity of the phosgenation reaction depends to a large extent on the amine concentration and the excess of phosgene. Phosgene is preferably used in a large molar excess while the amines to be phosgenated are used in a highly diluted form. The molar excess of phosgene is generally from 100 to 2000%, preferably from 100 to 1000%. The amine concentration, based on the total quantity of amine and solvent is from 0.1 to 15 wt %, preferably 5 to 10 wt %.

The solvents used may be any inert organic liquids or mixtures thereof having a boiling point from 60° to 250° C., i.e. halogenated hydrocarbons, aromatic compounds, hydroaromatic compounds and their chlorine compounds. Xylene, mesitylene, chlorobenzene, dichlorobenzene, trichlorobenzene, chloronaphthalene and dichloroethane are examples of suitable solvents.

The reaction may be carried out either in a single stage by hot phosgenation at temperatures from 100° to 250° C. or in two stages by cold/hot phosgenation at temperatures from −20° to 250° C. under normal pressure.

When free amines are used as starting compounds (phosgenation of base), ammonium carbamic acid chloride is first prepared at temperatures from −20° to 60°

C. and this then continues to react with phosgene at temperatures from 20° to 250° C. to form the polyisocyanate.

Purification of the products of the phosgenation process is generally carried out after dephosgenation, by evaporation of the solvent followed by distillation at reduced pressure.

The products of the process of the present invention, (i.e. the new triisocyanates) are obtained in high yields as colorless to yellow, low viscosity liquids and constitute valuable starting components for the production of polyurethanes by the isocyanate polyaddition process. The position and/or stereoisomerism of the triisocyanates corresponds to a large extent to the isomerism of the triamines used for phosgenation. The triisocyanate mixtures obtained by the process of the present invention generally need not be separated into individual position and/or stereoisomers because they may be used directly for the production of polyisocyanate addition products. Any diisocyanates or other by-products (in particular phosgenation products of triamines having a diphenylmethane or dicyclohexylmethane structure) present together with the triisocyanate of the present invention may however be partly or completely removed by distillation. For many applications of the triisocyanates of the present invention, however, preparation of such a pure product is not necessary. The corresponding polyisocyanate mixtures which contain, for example, at least 50 wt %, preferably at least 80 wt % of polyisocyanates corresponding to formula (I) are also valuable new starting materials for polyurethane chemistry. The triisocyanates of the present invention or mixtures thereof with the above-mentioned by-products containing at least 50 wt %, preferably at least 80 wt % of triisocyanates of formula (I) according to the invention may be used particularly advantageously for the production of polyurethane lacquers or coating materials. These triisocyanates may be used instead of or together with the previously used polyisocyanates in the known processes for the production of such synthetic resins. The new triisocyanates or polyisocyanate mixtures are particularly advantageously used on the basis of the prepolymer principle for producing the polyurethanes of the type exemplified above.

The following examples serve to explain the invention in more detail. All percentages are percentages by weight unless otherwise indicated. Analysis of the distribution of isomers in the intermediate products and end products was carried out gas chromatographically.

EXAMPLES

EXAMPLE 1

(1a) 350 g of an amine mixture made up of 1.4% of 4,4'-diaminodiphenylmethane, 10.2% of 4,6,2'-triamino-3-methyl-diphenylmethane, 6.8% of 2,6,4'-triamino-3-methyl-diphenylmethane, 78.7% of 4,6,4'-triamino-3-methyl-diphenylmethane and 2.9% of other aromatic polyamines were introduced into a 700 ml stirrer autoclave together with 35 g of ruthenium catalyst on aluminum oxide carrier (5% Ru). After repeated flushing with nitrogen, 35 g of liquid ammonia were pumped into the autoclave and the mixture was hydrogenated at 140° C. and 275 bar until, after a reaction time of 14.7 hours, the quantity of hydrogen theoretically required for the desired partial hydrogenation had been used up. The autoclave was then cooled to 70° C., the pressure was released and the product was taken up in 350 ml of methanol. The catalyst was filtered off and washed with methanol, and the combined filtrates were distilled. 299.5 g of crude product having the composition indicated below distilled off at a boiling temperature of 110° to 220° C./0.4 to 1 mbar:

3.4% of diamino-methyl-dicyclohexylmethane (isomeric mixture), 4.4% of diamino-methylbenzyl-cyclohexane (isomeric mixture), 4.3% of triamino-methyl-dicyclohexylmethane (isomeric mixture), 82.8% of diamino-methylbenzyl-cyclohexylmethane (isomeric mixture), 1.8% of triamino-methyl-diphenylmethane (isomeric mixture) and 3.3% of unknown polyamines. (1b) 280 g of the crude product from (1a) dissolved in 2 liters of chlorobenzene were added dropwise at 0° C. to a solution of 600 g of phosgene in 2 liters of chlorobenzene with stirring and cooling so that the reaction temperature did not rise above 0° C. The resulting suspension was heated to reflux while 300 g/h of phosgene were introduced. Boiling of the reaction mixture was then continued under the same conditions for an additional 4 hours. A clear solution was obtained, which was then gassed with phosgene under reflux conditions for another 2 hours. The solution was dephosgenated by the introduction of nitrogen, the solvent was distilled off at reduced pressure and the product was distilled at 100° to 220° C./0.5 to 0.8 mbar. After renewed distillation, 222 g of a liquid boiling at 155° to 170° C./0.1 mbar were obtained. According to gas chromographic and mass spectroscopic investigation, the liquid had the following composition:

3.4% of diisocyanato-methylbenzyl-cyclohexane (isomeric mixture), 81.5% of diisocyanato-methylbenzyl-cyclohexylisocyanate (isomeric mixture), 4.4% of triisocyanato-methyl-diphenylmethane (isomeric mixture) and 10.7% of unknown polyisocyanates.

The product had an isocyanate content of 38.7% and a viscosity of 180 mPa.sec/25° C.

EXAMPLE 2

A mixture of 97.9% of diamino-methylbenzyl-cyclohexylamine (isomeric mixture) and 2.1% of triamino-methyl-diphenylmethane (isomeric mixture) was obtained by nitration of a methyl-diphenylmethane isomeric mixture, catalytic hydrogenation of the nitro groups and hydrogenation at the nucleus as described in Example (1a) followed by working up by distillation. 175 g of this mixture were dissolved in 2 liters of anhydrous chlorobenzene. The amine solution was slowly introduced dropwise into a solution of 450 g of phosgene in 2 liters of chlorobenzene at −10° C. with stirring. A pale colored suspension formed, which was then slowly heated while phosgene was introduced at the rate of 300 g/h. At a reaction temperature of 60° C., vigorous evolution of hydrogen chloride occurred and the suspension assumed an orange color and turned into a clear solution at 125° C. After 1½ hours' boiling, the stream of phosgene was stopped and replaced by a stream of nitrogen introduced in the course of one hour. The solvent was evaporated off and 190 g of crude isocyanate were obtained after flash distillation at 180° to 200° C./0.2 to 0.3 mbar. After renewed distillation at reduced pressure, 185 g of diisocyanato-methylbenzylcyclohexyl isocyanate (isomeric mixture) were obtained. This product contained, based on the total mixture, 4.9% of diisocyanates with benzyl-cyclohexane structure, and was characterized by the following data:
Isocyanate content: 39.8%
Content in hydrolyzable chlorine: 0.04%
Boiling point: 158° to 162° C./0.05 mbar
Viscosity: 203° mPas/25° C.

EXAMPLE 3

(3a) 380 g of a mixture made up of
0.4% of 2,6,4'-triaminodiphenylmethane,
9.8% of 2,4,2'-triaminodiphenylmethane,
89.8% of 2,4,4'-triaminodiphenylmethane,
380 ml of tert.-butanol and 38 g of ruthenium (5%) $Al_2O_3$ carrier catalyst were introduced into a 1.3 liter stirrer autoclave. After repeated flushing with nitrogen and hydrogen, hydrogen was forced in to a pressure of 100 bar and the mixture was heated to 140° C. Hydrogenation was then carried out at a pressure of 275 bar with vigorous stirring until, after 8.5 hours, the quantity of hydrogen theoretically required for the desired partial hydrogenation had been used up. The autoclave was then cooled to 60° C. and relieved of pressure, and the catalyst was suction filtered and the product subjected to flash distillation. 285 g of an amine mixture boiling at 155° to 220° C./0.6 mbar were obtained. This amine mixture was made up of 10.1% of diamino-dicyclohexylmethane, 29.0% of triamino-dicyclohexylmethane, 51.6% of diaminobenzyl-cyclohexylamine and 9.3% of other, unidentified amines. After fine distillation at 210° C./0.5 mbar, 136 g of diaminobenzyl-cyclohexylamine (isomeric mixture) containing 6.2% (based on the total mixture) of triamino-cyclohexylamine (isomeric mixture) were isolated.

(3b) 136 g of the amine mixture from (3a) were dissolved in 1 liter of anhydrous chlorobenzene. Carbon dioxide was then introduced until saturation point was reached. The resulting suspension was introduced dropwise at −10° C., with vigorous stirring, into a solution of 400 g of phosgene in 1 liter of chlorobenzene. The mixture was gassed with 15 liter of phosgene per hour and heated to reflux in the course of 75 minutes. The solid substance dissolved completely after 3.5 hours of stirring. The solution was phosgenated for an additional 2 hours, excess phosgene was then blown off with nitrogen and the chlorobenzene was distilled off. The crude product was freed from polymeric by-products by flash distillation under a vacuum of 1 mbar and then distilled again. 145 g of isocyanate boiling at 182° to 185° C./0.6 mbar were obtained. This isocyanate was 91.7% (76.8% of the theoretical amount) of diisocyanatobenzyl-cyclohexylisocyanate isomers, 2.2% of triisocyanato-dicyclohexylmethane isomers and 6.1% of unknown isocyanates. The isocyanate content was 41.8%, the hydrolyzable chlorine content 600 ppm and the viscosity was 98 mPa.s/25° C.

EXAMPLE 4

(4a) 253 g of 2,4,4'-triaminodiphenylmethane, 253 g of tert.-butanol and 25.3 g of $Ru/Al_2O_3$ catalyst were introduced into a 1.3 liter stirrer autoclave and the mixture was hydrogenated at 140° C./275 bar with vigorous stirring. The theoretically required quantity of hydrogen had been taken up after a reaction time of 10 hours. The autoclave was cooled to 60° C. and emptied. After removal of the catalyst by filtration and washing, the crude product was distilled off. 234 g of an amine mixture made up of 61.9% of 4-(2,4-diaminobenzyl)-cyclohexylamine, 30.7% of 2,4,4'-triaminodicyclohexylmethane, 3.5% of various diamino-dicyclohexylmethanes and 3.9% of unknown amines distilled off in the boiling range of 110° to 184° C./0.5 mbar. After fine distillation at 184° C./0.5 mbar, 137 g of 4-(2,4-diaminobenzyl)-cyclohexylamine were isolated. Based on the total mixture, this compound contained 4.4% of 2,4,4'-triamino-dicyclohexylmethane.

(4b) An ammonium carbamate suspension was prepared by the introduction of carbon dioxide into a solution of 136 g of the distilled polyamine mixture from (4a) in 1 liter of chlorobenzene. This suspension was added with stirring to a solution of 400 g of phosgene in 1 liter of chlorobenzene at −10° C. and the reaction mixture was stirred for 15 minutes and heated to reflux in the course of one hour while 15 liters of phosgene were introduced. The solid substance had dissolved completely after 2 hours of hot phosgenation. The mixture continued to be phosgenated for another 4 hours and was then dephosgenated by the introduction of nitrogen. The solvent was distilled off, the crude product was partially purified by flash distillation and distilled again at 185° C./0.6 mbar. 150 g of isocyanate having the following composition were isolated: 96.2% of 4-(2,4-diisocyanatobenzyl)-cyclohexylisocyanate,
2.8% of 2,4,4'-triisocyanato-dicyclohexylmethane and
1.0% of unknown polyisocyanates.

The product was characterized by the following data:
NCO-value: 42.0%
Hydrolyzable chlorine content: 30 ppm
Viscosity/25° C.: 98 mPa.s Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A triisocyanate corresponding to the formula

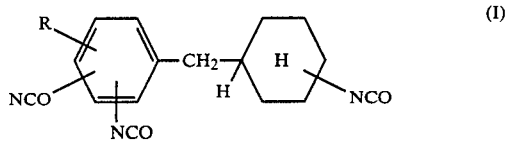

in which
R represents hydrogen or an alkyl group having from 1 to 4 carbon atoms.

2. The triisocyanate of claim 1 in the form of a mixture of position isomers and/or stereoisomers.

3. The triisocyanate of claim 2 in which R represents hydrogen or a methyl group.

4. A process for the production of the triisocyanates of claim 1 in which an araliphatic triamine corresponding to the formula

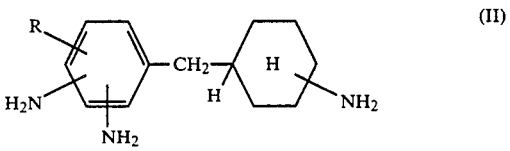

in which

R represents hydrogen or an alkyl group having from 1 to 4 carbon atoms or a salt thereof is phosgenated.

5. A process for the production of the triisocyanate isomer mixture of claim 2 in which an isomer mixture of araliphatic triamines corresponding to formula II or salts thereof is phosgenated.

6. A process for the production of isocyanate polyaddition products in which the triisocyanate of claim 1 is reacted with a material containing at least one isocyanate-reactive group.

7. A process for the production of isocyanate polyaddition products in which the triisocyanate isomer mixture of claim 2 is reacted with a material containing at least one isocyanate-reactive group.

* * * * *